(12) United States Patent
Bender et al.

(10) Patent No.: US 7,173,143 B2
(45) Date of Patent: Feb. 6, 2007

(54) INTEGRATED METHOD FOR SYNTHESIS PROPYLENE OXIDE

(75) Inventors: Michael Bender, Ludwigshafen (DE); Peter Zehner, Ludwigshafen (DE); Otto Machhammer, Mannheim (DE); Ulrich Mueller, Neustadt (DE); Klaus Harth, Altleiningen (DE); Goetz-Peter Schindler, Mannheim (DE); Henrik Junicke, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 145 days.

(21) Appl. No.: 10/526,045

(22) PCT Filed: Aug. 29, 2003

(86) PCT No.: PCT/EP03/09616
§ 371 (c)(1),
(2), (4) Date: Feb. 28, 2005

(87) PCT Pub. No.: WO2004/020423
PCT Pub. Date: Mar. 11, 2004

(65) Prior Publication Data
US 2005/0245751 A1  Nov. 3, 2005

(30) Foreign Application Priority Data
Aug. 30, 2002 (DE) ................. 102 40 129

(51) Int. Cl.
*C07D 301/12* (2006.01)
(52) U.S. Cl. ...................................... 549/531
(58) Field of Classification Search ................ 549/531
See application file for complete search history.

(56) References Cited

U.S. PATENT DOCUMENTS

| 3,798,283 A | 3/1974 | Bitar et al. |
| 4,009,252 A | 2/1977 | Izumi et al. |
| 4,336,238 A | 6/1982 | Dalton, Jr. et al. |
| 4,336,239 A | 6/1982 | Dalton, Jr. et al. |

(Continued)

FOREIGN PATENT DOCUMENTS

DE  197 23 950  12/1998

(Continued)

OTHER PUBLICATIONS

Sanfilippo, Domenico et al. "Fluidized Bed Reactors for Paraffins Dehydrogenation", Chemical Engineering Science, vol. 47, No. 9-11, pp. 2313-2318 1992.

*Primary Examiner*—Taofiq Solola
(74) *Attorney, Agent, or Firm*—Oblon, Spivak, McClelland, Maier & Neustadt, P.C.

(57) ABSTRACT

The present invention relates to an integrated process for the synthesis of propylene oxide, which comprises at least the following steps:

Figure 1:
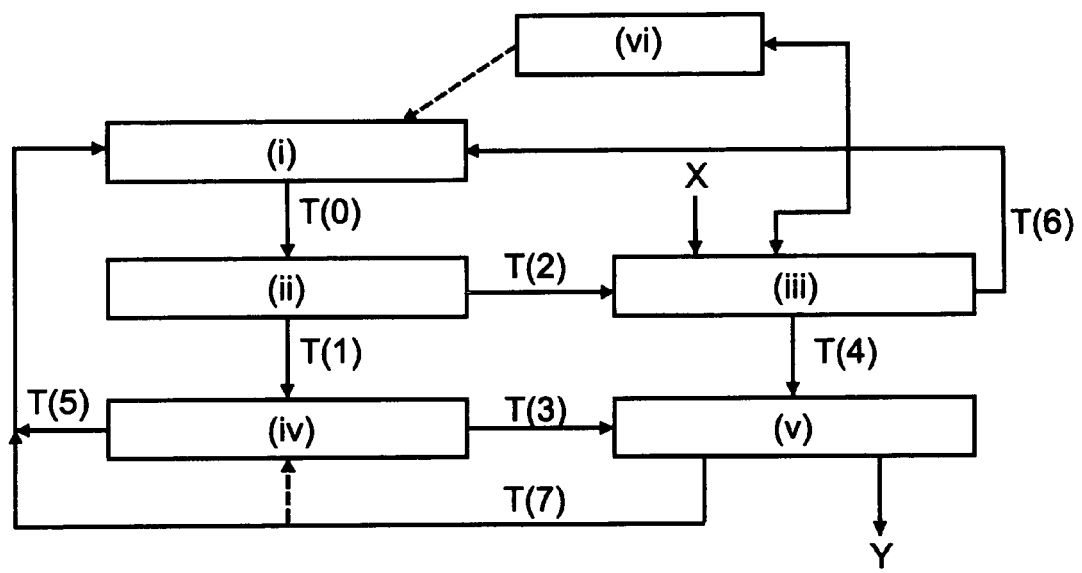

(i) dehydrogenation of propane to give a substream T(0) comprising at least propane, propene and hydrogen;
(ii) fractionation of the substream T(0) to give at least one gaseous hydrogen-rich substream T(2) and a substream T(1) comprising at least propene and propane;
(iii) synthesis of hydrogen peroxide using the substream T(2), giving a substream T (4) which is rich in hydrogen peroxide and a gaseous substream T(6);
(iv) fractionation of the substream T(1) to give at least one propane-rich substream T(5) and at least one propene-rich substream T(3);
(v) reaction of the at least one substream T(3) with substream T(4) to give propylene oxide.

10 Claims, 2 Drawing Sheets

U.S. PATENT DOCUMENTS

| | | |
|---|---|---|
| 4,389,390 A | 6/1983 | Dalton, Jr. et al. |
| 4,788,371 A | 11/1988 | Imai et al. |
| 4,886,928 A | 12/1989 | Imai et al. |
| 5,220,091 A | 6/1993 | Brinkmeyer et al. |
| 5,430,209 A | 7/1995 | Agaskar et al. |
| 5,430,220 A | 7/1995 | Khare et al. |
| 5,500,202 A | 3/1996 | Germain et al. |
| 5,527,979 A | 6/1996 | Agaskar et al. |
| 5,530,171 A | 6/1996 | Agaskar et al. |
| 5,563,314 A | 10/1996 | Agaskar et al. |
| 5,599,956 A | 2/1997 | Pujado et al. |
| 5,877,369 A | 3/1999 | Wu et al. |

FOREIGN PATENT DOCUMENTS

| | | |
|---|---|---|
| DE | 198 35 907 | 2/2000 |
| DE | 198 37 517 | 2/2000 |
| DE | 199 37 107 | 2/2001 |
| DE | 100 10 139 | 6/2001 |
| DE | 100 01 401 | 7/2001 |
| DE | 100 28 582 | 12/2001 |
| DE | 100 32 884 | 1/2002 |
| DE | 100 32 885 | 1/2002 |
| DE | 101 05 527 | 8/2002 |
| DE | 101 05 528 | 8/2002 |
| DE | 101 35 296 | 1/2003 |
| DE | 101 37 543 | 2/2003 |
| DE | 102 11 275 | 9/2003 |
| DE | 102 32 406 | 1/2004 |
| EP | 0 117 146 | 8/1984 |
| EP | 0 579 109 | 1/1994 |
| EP | 0 705 136 | 4/1996 |
| EP | 0 946 409 | 10/1999 |
| WO | 92/04277 | 3/1992 |
| WO | 98/55430 | 12/1998 |
| WO | 99/29420 | 6/1999 |
| WO | 99/46039 | 9/1999 |
| WO | 00/10961 | 3/2000 |
| WO | 00/20404 | 4/2000 |
| WO | 02/085875 | 10/2002 |

INTEGRATED METHOD FOR SYNTHESIS PROPYLENE OXIDE

The present invention relates to an integrated process for the synthesis of propylene oxide.

In the process of the present invention, the starting materials for the propylene synthesis are prepared via at least the steps propane dehydrogenation and direct synthesis of hydrogen peroxide and reacted to give propylene oxide.

The product propylene oxide forms the basis of a wide variety of chemical processes. The worldwide production capacity was about 2.9 million metric tons per annum in 1985, about 4.0 million metric tons per annum in 1993 and has grown continually since. Propylene oxide has hitherto been prepared predominantly by the chlorohydrin process and via indirect oxidation processes using hydroperoxides. The great disadvantages of these two processes are, for example, the wastewater problem and the by-product problem in the chlorohydrin process and the production of large amounts of oxygen-containing coproducts in a process via the indirect oxidation. These problems have in recent years led to development of alternative processes in the area of propylene oxide synthesis.

For example, close integration of chlorine production into the propylene oxide synthesis via the chlorohydrin process has enabled the economics to be improved.

In the propylene oxide synthesis by indirect oxidation methods, too, the disadvantageously large amount of coproducts has been able to be reduced in the propene oxidation, for example by use of percarboxylic acids which are prepared by means of hydrogen peroxide in a step preceding the propene oxidation, which improved the economic viability of this process.

Further advantageous developments in the field of propylene oxide synthesis are discussed, inter alia, in the documents DE 101 37 543.3, DE 101 35 296.4, DE 101 05 527.7 and DE 100 32 885.7.

Nevertheless, owing to the wide-ranging uses of propylene oxide, for example in the polymerization of alcohols, and the associated continual demand, there continues to be a need for a propylene oxide production process which makes it possible for the overall synthesis of propylene oxide, i.e. starting from the preparation of the starting materials through to recycling of the products other than propylene oxide obtained, to be made more economical and thus more competitive.

It is an object of the present invention to provide a further process for the integrated synthesis of propylene oxide.

We have found that this object is achieved by an integrated process for the synthesis of propylene oxide, which comprises at least the following steps:
(i) dehydrogenation of propane to give a substream T(0) comprising at least propane, propene and hydrogen;
(ii) fractionation of the substream T(0) to give at least one gaseous hydrogen-rich substream T(2) and a substream T(1) comprising at least propene and propane;
(iii) synthesis of hydrogen peroxide using the substream T(2), giving a substream T(4) which is rich in hydrogen peroxide and a gaseous substream T(6);
(iv) fractionation of the substream T(1) to give at least one propane-rich substream T(5) and at least one propene-rich substream T(3);
(v) reaction of the at least one substream T(3) with substream T(4) to give propylene oxide.

A preferred embodiment of the process, i.e. the essential steps making up the process, is shown schematically in FIG. 1 (FIG. 1).

The present invention further provides an extended integrated process for the synthesis of propylene oxide, which comprises at least the following steps:
(a) dehydrogenation of propane to give a substream T(0) comprising at least propane, propene and hydrogen;
(b) fractionation of the substream T(0) to give at least one gaseous hydrogen-rich substream T(2) and a substream T(1) comprising at least propene and propane;
(c) fractionation of the substream T(1) to give at least one propane-rich substream T(5) and at least one propene-rich substream T(3);
(d) separation of the substream T(5) into at least the substreams T(5*a*) and T (5*b*);
(e) synthesis of hydrogen peroxide using the substream T(2) which is combined with at least the substream T(5*a*), giving a substream T(4) which is rich in hydrogen peroxide and a gaseous substream T(6*a*);
(f) recirculation of the substream T(6*a*) to step (a);
(g) reaction of the at least one substream T(3) with substream T(4) to give propylene oxide.

Figure 2:
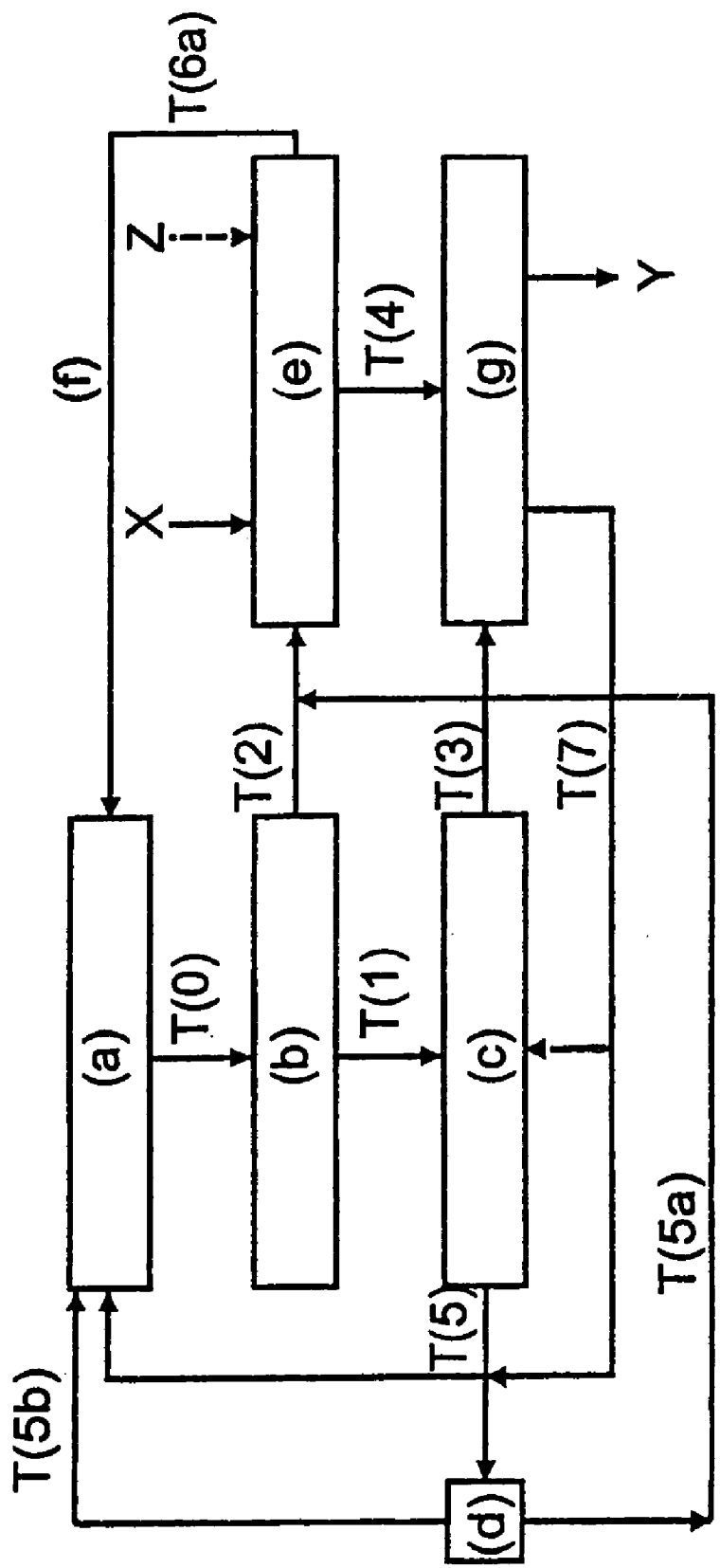

A preferred embodiment of the extended integrated process for the synthesis of propylene oxide, i.e. the essential steps making up the process, is shown schematically in FIG. 2 (FIG. 2).

Step (i) or step (a) of the process of the present invention comprises dehydrogenation of propane to give a substream T(0) comprising at least propane, propene and hydrogen.

The dehydrogenation of propane in the process of the present invention can in principle be carried out by all methods known to those skilled in the art for the dehydrogenation of propane, for example steam cracking or catalytic cracking and also, in particular, catalytic dehydrogenation in the presence or absence of oxygen or oxygen-containing mixtures.

To achieve economically viable conversions, based on a single pass, in the dehydrogenation of propane, it is necessary to work at relatively high reaction temperatures. These are generally from 300 to 700° C.

Since the dehydrogenation, i.e. the cleavage of a C—H bond, is generally less favored kinetically than cracking, i.e. the cleavage of a C—C bond, it is preferably carried out over catalysts which are selective for dehydrogenation. These are usually of such a nature that they give a good yield of dehydrogenation products in the absence of oxygen in the abovementioned temperature range. At a space velocity of propane over the catalysts of, for example, 1000 $h^{-1}$ (i.e. standard liters of propane per liter of catalyst and hour), the yield of propylene is generally at least 30 mol % based on the propane used in a single pass. By-products such as methane, ethylene and ethane are formed in only subordinate amounts.

Since dehydrogenation of propane proceeds with an increase in volume, the conversion can in principle be increased by reducing the partial pressure of the products. This can be achieved in a simple manner by, for example, carrying out the dehydrogenation under reduced pressure and/or with introduction of essentially inert diluent gases. For the purposes of the present invention, steam is such a preferred inert diluent gas. Further diluent gases suitable for the dehydrogenation of propane are, for example, $CO_2$, $N_2$ and noble gases such as He, Ne and Ar.

Dilution with steam generally gives the further advantage of reduced carbonization of the catalysts used, since the steam reacts with any carbon deposits being formed according to the principle of coal gasification. Furthermore, steam can easily be separated partly or completely from the product mixture. Accordingly, when steam is used as diluent in the propane dehydrogenation in the process of the present invention, it can be separated off from the product stream T(0) by, for example, condensation.

In the dehydrogenation of propane in step (i) or step (a), it is in principle possible to use all dehydrogenation catalysts known to those skilled in the art for this purpose. For example, catalysts which are oxidic in nature and comprise chromium oxide and/or aluminum oxide or catalysts comprising at least one substantially noble metal, e.g. platinum, deposited on at least one generally oxidic support can be used.

The dehydrogenation catalysts described in the following documents can, inter alia, be used for the purposes of the present invention: WO 99/46039, U.S. Pat. No. 4,788,371, EP-A 705 136, WO 99/29420, U.S. Pat. Nos. 5,220,901, 5,430,220, 5,877,469, EP-A 117 146, DE 199 37 105, and DE 199 37 107.

In particular, the dehydrogenation catalysts described in the examples of DE 199 37 107 can be used. These are dehydrogenation catalysts comprising from 10 to 99.9% by weight of zirconium dioxide, from 0 to 60% by weight of aluminum oxide, silicon dioxide and/or titanium dioxide and from 0.1 to 10% by weight of at least one element of the first or second main group, the third or eighth transition group of the Periodic Table of the Elements, lanthanum and/or tin, with the proviso that the sum of the percentages by weight is 100.

To carry out the dehydrogenation of propane in the process of the present invention, it is in principle possible to use all reactor types and process variants known to those skilled in the art for this purpose, for example those which are described in the documents cited in the previous section in respect of the dehydrogenation catalysts.

For example, the propane used in the dehydrogenation of propane can be oxidized homogeneously to propene in the presence of molecular oxygen at elevated temperature as described in U.S. Pat. No. 3,798,283. For the purposes of the invention, the oxygen source can be either pure oxygen or a mixture of oxygen and inert gas.

The heterogeneously catalyzed oxydehydrogenation of propane to propene described in DE 195 30 454 can also be employed for the propane dehydrogenation. Here, the propane is converted into propene in the presence of air or an oxygen-containing mixture in a fixed-bed or fluidized-bed reactor containing catalyst.

For the purposes of the invention, it is also possible to convert propane into propene by homogeneously and/or heterogeneously catalyzed oxydehydrogenation by means of molecular oxygen in a manner analogous to the process described in DE 198 37 517.

In principle, all oxydehydrogenation processes which can be used for the purposes of the invention can be carried out in at least one reaction vessel containing catalytically active substance, for example a fixed-bed reactor or a fluidized-bed reactor. In this reactor, the propane is converted into propene over the catalytically active substance used in each case via reaction steps known to those skilled in the art.

A further possibility for the dehydrogenation of propane in the process of the present invention is the Oleflex™ process or methods similar thereto. In this process, the feed propane, admixed with pure or recycled hydrogen, is converted into propene in at least one reactor comprising at least one suitable catalyst bed.

In principle, propane can be partly or virtually completely dehydrogenated to propene in the presence of a dehydrogenation catalyst. Partial dehydrogenation forms a product gas mixture comprising unreacted propane and the propene formed together with secondary constituents such as hydrogen, water, further cracking products of propane, CO and $CO_2$. The dehydrogenation of propane can be carried out with or without an oxygen-containing gas as cofeed.

The partial heterogeneously catalyzed dehydrogenation of propane generally proceeds endothermically, i.e. the heat/energy required to set the reaction temperature required is introduced into the reaction gas before and/or during the catalytic dehydrogenation.

Owing to the relatively high reaction temperature required for the propane dehydrogenation, formation of small amounts of high-boiling high molecular weight organic compounds, sometimes even carbon, can occur and these may deposit on the catalyst surface. To minimize or avoid this unfavorable accompanying phenomenon, the starting material propane can be diluted with hydrogen in the process of the present invention, so that any carbon formed can be largely eliminated according to the principle of coal hydrogenation.

A comprehensive description of reactor types and modes of operation which are suitable in principle for the dehydrogenation of propane in the process of the present invention is given in "Catalytica® Studies Division, Oxydative Dehydrogenation and Alternative Dehydrogenation Processes, Study No. 4192 OD, 1993, 430, Ferguson Drive, Mountain View, Calif., 94043–5272, U.S.A.".

A suitable form of reactor for step (i) or step (a) of the process of the present invention is a fixed-bed tube reactor or shell-and-tube reactor. In this, the catalyst is present as a fixed bed in a reaction tube or in a bundle of reaction tubes. The dehydrogenation of propane can be carried out in the absence of oxygen or, when suitable catalyst formulations are employed, with introduction of oxygen as cofeed. The reaction tubes can be heated by a gas, for example a hydrocarbon such as methane, being burnt in the space surrounding the reaction tubes.

In a preferred embodiment of the integrated process for the synthesis of propylene oxide, all or some of the gaseous substream T(6) from step (iii) can be burnt to produce energy and the energy can be used in the propane dehydrogenation, for example for indirect heating of the reaction tubes in question.

It is advantageous to apply this indirect form of heating only to the first about 20–30% of the length of the fixed catalyst bed and to heat the remaining length of the bed to the required reaction temperature by means of the radiant heat liberated in the indirect heating.

Since the catalyst is generally, depending on the space velocity of the gas and the conversion, deactivated more or less rapidly by carbonization, it is advantageous to generate it at regular intervals. The substream T(6) from step (iii) can be used for regeneration in the process of the present invention. Further regeneration methods which can be used according to the present invention are described in WO 98/55430 and the prior art cited therein.

In a further embodiment of the present invention, the dehydrogenation of propane can be carried out in a moving bed reactor. The moving catalyst bed can be accommodated in, for example, a radial flow reactor. In this, the catalyst slowly moves from the top downward, while the reaction gas mixture flows radially. Since the reactors in this process are operated pseudoadiabatically it is advantageous to employ a plurality of reactors connected in series.

The mixture entering each reactor can be heated to the required reaction temperature upstream of the reactor by indirect heating. It is likewise possible to heat the gas mixture entering each reactor to the required reaction temperature by combustion of hydrogen in the presence of added oxygen (autothermal operation). Both in the integrated process and the extended integrated process for the synthesis of propylene oxide according to the present invention, it is advantageous to use all or some of the substream T(6) or T(6*a*) from step (iii) for heating the inflowing gas mixture or for aiding autothermal operation of the propane dehydrogenation of step (a).

Furthermore, the use of a plurality of reactors enables large differences in the temperature of the reaction gas mixture between reactor inlet and reactor outlet to be avoided and high total conversions to be achieved. When the catalyst bed has left the moving bed reactor, it is passed to regeneration and subsequently reused. The regeneration of the catalyst in a moving bed reactor is generally carried out continuously. Here, all or part of the exhausted catalyst is discharged at the end of a reactor, in particular at the end of the last reactor, and passed to at least one subsequent regeneration step. After regeneration, the catalyst is returned to the beginning of a reactor, in particular the beginning of the first reactor.

The heterogeneously catalyzed dehydrogenation of propane carried out in a fluidized bed, the operation of which is described in "Chem. Eng. Sci. 1992 b 47 (9–11), 2313", is likewise a possible way of carrying out the dehydrogenation of propane for the purposes of the present invention. In this process, the propane does not have to be diluted. It is advantageous to operate two fluidized beds side by side in the dehydrogenation, so that one of them can generally be in the state of regeneration. The regeneration of the fluidized beds can, in a preferred embodiment of the integrated process for the synthesis of propylene oxide, be carried out using the substream T(6) from step (iii). The heat required for the dehydrogenation is introduced into the reaction system by the dehydrogenation catalyst being preheated to the reaction temperature. In a preferred embodiment of the present invention, preheating can also be carried out by means of the energy produced by burning all or some of the substream T(6) from step (iii).

In a further embodiment of the present invention, the introduction of an oxygen-containing cofeed makes it possible to dispense with the preheater or intermediate heaters or the indirect heating via the reactor surfaces and to generate all or part of the necessary heat directly in the reactor system by combustion of hydrogen and/or hydrocarbons in the presence of molecular oxygen. In such an embodiment, the substream T(6*a*) from step (e) of the novel extended integrated process for the synthesis of propylene oxide is, in a further step (f), recirculated to the propane dehydrogenation step (a), thus making largely autothermal operation of the propane dehydrogenation possible. If appropriate, a hydrogen-containing cofeed can be additionally mixed in.

Carrying out the dehydrogenation of propane in a tray reactor is another possibility for the purposes of the present invention. A tray reactor comprises one or more successive catalyst beds through which the reaction gas preferably flows radially or axially. In general, such a tray reactor is operated using a fixed catalyst bed. In the simplest case, the fixed catalyst beds are arranged axially in a shaft furnace reactor or in the annular gaps of concentric mesh cylinders. One shaft furnace reactor corresponds to one tray. In a procedure without oxygen as cofeed, the reaction gas mixture is subjected to intermediate heating on its way from one catalyst bed to the next catalyst bed in the tray reactor, for example by passing it over heat exchanger surfaces heated by means of hot gases or by passing it through tubes heated by means of hot combustion gases.

In a procedure using oxygen, a limited amount, depending on the dehydrogenation catalyst used, of the hydrocarbons present in the reaction gas, possibly also carbon deposited on the catalyst surface and/or hydrogen formed during the propane dehydrogenation and/or added to the reaction gas is burnt. The heat of reaction liberated in this way also makes it possible to operate the propane dehydrogenation autothermally.

It is also possible, in a further embodiment of the process of the present invention, to carry out step (a), viz. the dehydrogenation of propane, autothermally. For this purpose, an oxygen-containing gas is additionally mixed into the reaction mixture of the propane dehydrogenation in at least one reaction zone and the hydrogen present in the reaction gas mixture is burnt, thus generating at least part of the necessary heat of dehydrogenation directly in the reaction mixture in the reaction zone or zones.

The dehydrogenation of propane is preferably carried out in the circulation mode described in DE 102 11 275.4.

To operate the propane dehydrogenation step (a) autothermally in the novel extended integrated process for the synthesis of propylene oxide, all or some of the gaseous, hydrogen-containing substream T(6*a*) obtained in step (e) is recirculated to step (a) and burnt.

Regulating the amount of oxygen added via substream T(6*a*) makes it possible to control the reaction temperature in step (a). At the same time, the selectivity of the propane dehydrogenation in step (a) can be controlled by regulating the amount of hydrogen added via substream T(6*a*).

The quantity of heat provided for the dehydrogenation of propane to propene, which is generated by combustion of the hydrogen present in the reaction gas mixture and possibly hydrocarbons present in the reaction gas mixture and/or carbon present in the form of carbon deposits, is regulated via the amount of oxygen-containing gas added to the reaction gas mixture.

Additional oxygen introduced can be fed in either as molecular oxygen or as oxygen-containing gas, e.g. in admixture with inert gases.

In a preferred embodiment of the invention, additionally introduced molecular oxygen is employed for this purpose.

In a further preferred embodiment of the present invention, the oxygen-containing gas in question is the substream T(6*a*) from the hydrogen peroxide synthesis in step (e).

The inert gases and the resulting combustion gases generally have an additional diluent effect and thus promote the heterogeneously catalyzed dehydrogenation. The hydrogen burnt to generate heat can be the hydrogen formed in the hydrocarbon dehydrogenation or additional hydrogen added to the reaction gas mixture, for example via the hydrogen-containing substream T(6*a*) from step (e) in the novel extended integrated process for the synthesis of propylene oxide.

The amount of hydrogen added is basically such that the molar ratio of $H_2/O_2$ in the reaction gas mixture directly after the feed point is from 0 to 10 mol/mol. This applies both in the case of multistage reactors and for the intermediate introduction of hydrogen and oxygen. The hydrogen combustion in question occurs catalytically, with the dehydrogenation catalyst used generally also catalyzing the combustion of the hydrocarbons and the combustion of hydrogen in the presence of oxygen, so that in principle no specific oxidation catalyst different from this is necessary. However, it is of course also possible to employ one or more oxidation catalysts. These selectively catalyze the combustion of hydrogen to oxygen in the presence of hydrocarbons. As a result, the combustion of hydrocarbons with oxygen to form CO, $CO_2$ and $H_2O$ occurs to only a subordinate extent: which has a significant positive effect on the achieved selectivity of the formation of propene. The dehydrogenation catalyst and the oxidation catalyst are preferably present in different reaction zones.

In the case of a multistage reaction, the oxidation catalyst can be present in only one reaction zone, in a plurality of reaction zones or in all reaction zones.

The catalyst which selectively catalyzes the oxidation of hydrogen in the presence of hydrocarbons is preferably located in places at which the oxygen partial pressures are higher than at other places in the reactor, in particular in the vicinity of the feed point for the oxygen-containing gas. Oxygen-containing gas and/or hydrogen can be introduced at one or more points on the reactor.

A preferred catalyst which selectively catalyzes the use of hydrogen generally comprises oxides or phosphates selected from the group consisting of the oxides and phosphates of germanium, tin, lead, arsenic, antimony and bismuth.

A more preferred catalyst which catalyzes the combustion of hydrogen comprises at least one noble metal of transition group VIII of the Periodic Table of the Elements. Examples of such catalysts are described, for example, in the following documents:

U.S. Pat. Nos. 4,788,371, 4,886,928, 5,430,209, 5,530,171, 5,527,979 and 5,563,314.

The dehydrogenation of propane is preferably carried out in the presence of steam. The steam added serves as heat transfer medium and aids the gasification of organic deposits on the catalysts, thus countering carbonization of the catalysts and enabling the operating life of the catalyst to be increased. The organic deposits are in this case converted into carbon monoxide and carbon dioxide.

For the purposes of the present invention, the dehydrogenated of propane is preferably carried out in tray processes, with largely autothermal and therefore cost-effective operation being made possible in the extended integrated process for the synthesis of propylene oxide by combustion of the hydrogen introduced via the substream T(6a).

In the process of the invention, the quality of the propane feed is in principle not critical. The propane used can be fresh or recycled propane and may further comprise additional by-products which have no significant influence on the dehydrogenation process.

The propane dehydrogenation can also be carried out continuously or batchwise.

In a preferred embodiment of the propane dehydrogenation in step (i) of the process of the present invention, the substream T(0) produced in this step comprises at least propene, propane and hydrogen. Furthermore, T(0) can further comprise gases from the group consisting of $N_2$, $H_2O$, methane, ethane, ethylene, CO and $CO_2$, either individually or as mixtures of two or more gases from this group, as by-products.

In the process of the present invention, the ratio of propane to propene in substream T(0) is in the range from 0.1 to 10, preferably from 0.5 to 5, particularly preferably from 1.0 to 2.0. The ratio of hydrogen to propene in substream T(0) is in the range from 0 to 1.5, preferably from 0.3 to 1.3, particularly preferably about 1.1.

In a mode of operation using oxygen as cofeed, i.e. additionally introduced oxygen or circulated gas from step (iii), viz. the hydrogen peroxide synthesis (T(6) or T(6a)), the hydrogen to propene ratio is preferably from 0.4 to 2.0.

In principle, all or some of substream T(0) is transferred via suitable means known to those skilled in the art, for example lines in the form of pipes, to step (ii) or, in the case of the extended integrated process for the synthesis of propylene oxide, to step (b).

Furthermore, it is also possible for substream T(0) to be fed to a separation apparatus in an intermediate step following step (i) or step (a). In this, any by-products which have been formed in the propane dehydrogenation and may be present in T(0) can be separated off.

Step (ii) or step (b) comprises the fractionation of substream T(0) to give at least one gaseous hydrogen-rich substream T(2) and a liquid substream T(1) comprising at least propene and propane.

The fractionation of the substream T(0) can, for the purposes of the invention, in principle be carried out by all methods which are known to those skilled in the art and are technically possible in the present case and using the apparatuses which are suitable for the respective method. For example, the fractionation can be carried out by means of the apparatus described in DE 100 28 582.1.

Thus, the separation of T(1) from substream T(0) in step (ii) or step (b) can be carried out by bringing the preferably cooled substream T(0) into contact with a preferably hydrophobic organic solvent in which the constituents propane and propene present in T(1) are preferentially absorbed.

Subsequent desorption, rectification and/or possibly stripping with an inert gas and/or an oxygen-containing gas, but for the purposes of the present invention preferably molecular oxygen, allows at least the constituents propane and propene present in T(1) to be recovered.

The substream T(2) which comprises at least hydrogen represents the tailgas from the absorption. The absorption can be carried out either in columns or in rotary absorbers. These can be operated in cocurrent or in countercurrent. Suitable absorption columns are, for example, tray columns, columns containing structured packing and columns containing random packing. Of course, trickle and sprayed towers, granite block absorbers, surface absorbers such as thick film absorbers and thin film absorbers and also rotary columns, plate scrubbers, crossed spray scrubbers and rotary scrubbers are also possible.

In principle, all absorption media which are known to those skilled in the art and appear suitable for this purpose can be used. For the purposes of the present invention, preference is given to using relatively nonpolar organic solvents which preferably have no externally acting polar groups, e.g. aliphatic (e.g. $C_8$–$C_{18}$-alkanes), also aromatic hydrocarbons such as middle oil fractions from paraffin distillation, or ethers having bulky groups on the oxygen atom. Mixtures of two or more of the solvents mentioned are also useful. Further solvents or solvent mixtures which can be used as absorption media in the process of the present invention are listed in DE 100 28 582.1.

A solvent mixture which is preferably used as absorption medium for the purposes of the present invention comprises biphenyl and diphenyl ether, preferably having the azeotropic composition, in particular a mixture of about 25% by weight of biphenyl and about 75% by weight of diphenyl ether (Diphyl®).

However, for the purposes of the present invention, substream T(0) is preferably fractionated by condensation to give the substreams T(1) and T(2).

Thus, in the process of the present invention, the $C_3$ components of the substream T(0) can be wholly or partly condensed by, for example, use of heat exchangers, for example surface condensers or condensers with direct or indirect air cooling.

Preference is given to using one or more shell- and-tube heat exchangers in the process of the present invention. In this case, cooling within the heat exchangers can be carried out using either air, water or another suitable medium.

Thus, the substream T(0) can be wholly or partly condensed in step (ii) or step (b). Preference is given to virtually complete condensation of the $C_3$ components such as propene and propane present in the substream T(0).

In the process of the present invention, more than 90%, preferably more than 95%, particularly preferably more than 99%, of the $C_3$ components present in T(0) are separated off as substream T(1) by means of the abovementioned fractionation methods in step (ii) or step (b).

Substream T(1), which comprises at least the $C_3$ components propene and propane, is passed via suitable lines known to those skilled in the art to step (iv) or step (c).

The gaseous substream T(2) which remains comprises hydrogen as main component and possibly also a variable proportion of $C_3$ components and possibly further gaseous, low-boiling components. The proportion of $C_3$ components present in T(2) can be controlled via the conditions in step (ii) or step (b). The gas phase in question is conveyed as substream T (2) via lines known to those skilled in the art to step (iii). In the novel extended process for the synthesis of propylene oxide, T(2) is combined with a substream T(5*a*) and conveyed via lines known to those skilled in the art to step (e).

In the integrated process for the synthesis of propylene oxide, the gaseous substream T(2) from step (ii) can have a ratio of hydrogen to $C_3$ components in the range of at least 90–95:10–5, preferably at least 99:1 and particularly preferably at least 99.9:0.1.

The liquid substream T(1) which is produced in step (ii) or step (b) and comprises at least propene and propane is fractionated in a further step (iv) or step (c) to give at least one propane-rich substream T(5) and at least one propene-rich substream T(3).

The fractionation of the substream T(1) can be carried out by all methods which are known to those skilled in the art for this purpose, but is preferably carried out by thermal methods such as distillation and/or rectification.

In principle, all distillation processes suitable for the fractionation of the substream T(1) to give a propane-rich substream and a propene-rich substream can be used.

The fractionation unit used for this purpose in the process of the present invention basically comprises all constituent parts which are known to those skilled in the art and are necessary to separate mixtures by fractional distillation into at least one propane-rich fraction and at least one propene-rich fraction. However, for the purposes of the present invention, the substream T(1) is preferably fractionated by rectification to give a propane-rich substream and a propene-rich substream. In this process, the enrichment or separation of the liquid mixture occurs essentially by mass transfer between vapor and boiling liquid flowing in countercurrent. The rectification is carried out in one or more rectification columns which consist essentially of tubular separation columns and also vaporizers and a condenser at the upper end (top) of the respective column.

In the process of the present invention, more than 80%, preferably at least 90%, particularly preferably at least 95%, of the propene present in T(1) is separated off in the substream T(3) in step (iv) or step (c). This propene-rich substream T(3) is passed to the further step (v) or step (g) via suitable lines.

In the process of the present invention, the propane-rich substream T(5) from step (iv) can be recirculated to step (i).

It is also possible for the propane-rich substream T(5) to be worked up by further methods known to those skilled in the art before it is fed into step (i), e.g. it can be enriched in the propane present therein before being fed into step (i).

Accordingly, the present invention also provides a process of the above-described type in which the propane-rich substream T(5) is fed to step (i).

In the extended integrated process for the synthesis of propylene oxide, the propane-rich substream T(5) produced in step (c) is transferred via suitable lines to step (d).

In step (d), the substream T(5) is separated into at least the substreams T(5*a*) and T(5*b*). In a preferred embodiment of the present invention, the substream T(5) is purified to separate off by-products present in addition to propane before it is divided. This purification can be carried out by all methods known to those skilled in the art for this purpose, e.g. distillation or absorption processes.

The separation of the substream T(5) is carried out by all methods available to those skilled in the art for this purpose, for example by division by means of a multiway valve. Separation with simultaneous purification, for example by means of distillation, is also possible.

Basically, in step (d), T(5) is separated into two substreams T(5*a*) and T(5*b*) which may comprise identical or different amounts of propane.

Substream T(5*b*) is, according to the present invention, recirculated to step (a) via lines known to those skilled in the art.

Substream T(5*a*) can, if appropriate, be purified again and is then combined with the hydrogen-containing substream T(2) from step (b) and transferred to step (e).

Step (iii) or step (e) of the process of the present invention comprises the synthesis of hydrogen peroxide.

In step (iii) the hydrogen-containing substream T(2) is reacted with introduced oxygen (X in FIG. 1), for example in the form of air, giving a substream T(4) which is rich in hydrogen peroxide and a gaseous substream T(6).

In step (e) of the extended integrated process for the synthesis of propylene oxide, the propane-containing substream T(5*a*), which has been combined with the hydrogen-containing substream T(2) with an introduced oxygen-containing gas, e.g. air or molecular oxygen (X in FIG. 2) to give a substream T(4) which is rich in hydrogen peroxide and a gaseous substream T(6*a*).

In a preferred embodiment of the extended integrated process, oxygen is introduced in place of air. This avoids the accumulation and the associated purging of any interfering gases.

If desired, not only oxygen or air but also hydrogen can be introduced into step (iii) or step (e) by means of a suitable facility (Z in FIG. 1 and FIG. 2).

Essentially all processes for synthesizing hydrogen peroxide which are known to those skilled in the art can be used in step (iii) or step (e).

In a preferred embodiment of the processes of the present invention, hydrogen peroxide is prepared by direct synthesis from the elements. For the purposes of the present invention, it is possible to use all methods for the direct synthesis of hydrogen peroxide from the elements which are known by those skilled in the art.

In the extended integrated process for the synthesis of propylene oxide, the use of the combined substreams T(2)

and T(5*a*) in step (e) offers the advantage that it achieves a reduction in the amount of oxygen in the reaction mixture of the hydrogen peroxide synthesis to below the lower explosive limit (4% $H_2$ to 96% of $O_2$), thus increasing the safety of the process. The propane added via T(5*a*) is thus a safe gas buffer for the direct synthesis of hydrogen peroxide in this embodiment of the invention.

A further associated advantage is that an increase in the hydrogen concentration to a ratio of oxygen to hydrogen of 1 to 1 or above is made possible in this way. Since the space-time yield of the direct synthesis of hydrogen peroxide increases in proportion to the hydrogen concentration, this embodiment of the invention makes it possible to make the reactor dimensions smaller and thus also decrease the operating costs.

In step (e) of the novel extended process for the synthesis of propylene oxide, the amount of oxygen and hydrogen in the feed is adjusted so that the ratio in the substream T(6*a*) from this step is optimal for use in the propane dehydrogenation of step (a).

Accordingly, in the novel extended process for the synthesis of propylene oxide, the substream T(6*a*) from step (e) is recirculated to step (a) and thus makes it possible for the direct synthesis of propane to be operated autothermally, as described above.

This mode of operation thus makes it possible to dispense with circulated gas in the direct synthesis of hydrogen peroxide.

An example of a possible method of preparing hydrogen peroxide in the process of the present invention is the procedure disclosed in U.S. Pat. No. 4,009,252, in which hydrogen peroxide is formed from hydrogen and oxygen over palladium-containing catalysts. This reaction is carried out batchwise. WO 92/04277, too, describes a process which can be used for the purposes of the present invention and comprises reacting hydrogen with oxygen in a tube reactor charged with an aqueous catalyst suspension to give hydrogen peroxide. A further possible way of preparing hydrogen peroxide for the purposes of the present invention is the continuous process for preparing hydrogen peroxide which is described in U.S. Pat. No. 5,500,202 and EP-A 0 579 109 and comprises reacting $H_2O_2$ gas mixtures over a stationary, pulverulent catalyst in a trickle bed reactor.

A further process known from the prior art for preparing hydrogen peroxide which can be used for the purposes of the present invention is described in U.S. Pat. Nos. 4,336,238 and 4,336,239. In this process, the reaction and oxygen to form hydrogen peroxide is carried out over palladium-containing catalysts in organic solvents or solvent mixtures which may also comprise water. U.S. Pat. No. 4,389,390 describes a similar process in which the catalyst which has been leached from the support is recovered by means of activated carbon filters.

However, the process for preparing hydrogen peroxide solutions which has been developed by the applicant himself and is described in EP-A 0 946 409 is particularly preferably used for the purposes of the present invention. This process allows the safe preparation of hydrogen peroxide solutions having a hydrogen peroxide content of at least 2.5% by weight. In this process, hydrogen and oxygen are reacted continuously over catalysts comprising palladium as active component, with the reaction being carried out over shaped catalyst bodies in water and/or $C_1$–$C_3$-alkanols as reaction medium. The shaped catalyst bodies are preferably ordered catalyst packing (monoliths) and/or beds, or shaped bodies made up of meshes, for example metal meshes. In this preferred process, it is possible to use oxygen in the form of air.

In this process, the reaction is generally carried out in a flooded reactor. Water and/or $C_1$–$C_3$-alkanols, preferably water and/or methanol, serve as reaction medium. The reaction gas, which may comprise not only hydrogen and oxygen but also inert gases such as nitrogen or noble gases, generally has an $O_2$:$H_2$ ratio in the range from 1:100 to 100:1. It is possible to circulate the reaction gas. Reaction gas and reaction medium can be conveyed in cocurrent or in countercurrent relative to one another, preferably in cocurrent, with the liquid phase forming the continuous phase and the reaction gas forming the discontinuous phase. Preference is given to a vertical reactor construction (upright reactor) in which the reaction gas and reaction medium are preferably passed through the reactor in cocurrent from the bottom upward. Hydrogen can be introduced into the reactor via one or more intermediate feed points downstream of the feed point for the oxygen or air. The two-phase output from the reactor can be taken off at the upper end of the reactor and separated in a suitable separation vessel to give a substream T(4) which is rich in hydrogen peroxide and a gaseous substream T(6) or T(6*a*).

For the purposes of the present invention, the synthesis of hydrogen peroxide in step (iii) is carried out so that even when hydrogen/oxygen mixtures above the explosive range ($O_2$:$H_2$>20:1) are used, hydrogen-peroxide solutions having an $H_2O_2$ content above 2.5% by weight are obtained.

The substream T(4) which is rich in hydrogen peroxide comprises at least hydrogen peroxide and water. Substream T(4) may further comprise halides, acids, alcohols and further organic components and also sensitizers and promoters for the hydrogen peroxide synthesis, e.g. CO.

If appropriate, T(4) can be worked up further by methods known to those skilled in the art.

Accordingly, the invention also provides a process of the above-described type in which substream T(4) comprises at least hydrogen peroxide and water.

All or some of the gas phase T(6) can be burnt, either after compression in a suitable compressor or else directly, in a further step (vi) to generate energy and the energy can be utilized in the step (i).

Accordingly, the present invention also provides a process as described above in which all or some of the gaseous substream T(6) from step (iii), which comprises a mixture of hydrogen and oxygen, is burnt in a further step (vi) to generate energy and the energy is utilized in step (i).

This variant is particularly preferred when the substream T(6) from step (iii) comprises less than 4% of hydrogen in oxygen or less than 4% of oxygen in hydrogen.

The energy produced in step (vi) can be used in step (i) for heating the apparatuses used for the dehydrogenation of propane and/or for regeneration of the catalyst or catalysts used in the propane dehydrogenation.

Accordingly, the present invention also provides a process as described above in which the energy is utilized in step (i) for the following purposes, either individually or in combination with one another:

(aa) heating the apparatuses used in the dehydrogenation of propane;

(bb) regeneration of the catalyst or catalysts used in the propane dehydrogenation.

In a further embodiment of the present invention, substream T(6) can be recirculated either wholly or partly to step (iii).

To counter accumulation of inert compounds which may occur in the case of complete recirculation of T(6), a substream of T(6) is transferred from time to time or continuously during the process for utilization in step (i). This procedure is preferably chosen whenever the gaseous substream T(6) contains more than 0.5%, preferably more than 0.7%, particularly preferably more than 1%, of a mixture of hydrogen and oxygen.

Accordingly, the present invention also provides a process of the abovementioned type in which all or some of the gaseous substream T(6) from step (iii) which contains more than 1% of a mixture of hydrogen and oxygen is recirculated to step (iii).

In a further embodiment of the integrated process for the synthesis of propylene oxide, all or some of the gaseous substream T(6) from step (iii) can be recirculated to step (i). The advantage of this procedure is that the gaseous substream T(6) which, in this embodiment, comprises $C_3$ residues together with $H_2$ and $O_2$ in an $H_2:O_2$ ratio of from 1:100 to 100:1 can be used for regenerating the catalyst used in step (i) for dehydrogenation of propane. The regeneration is carried out essentially by burning off all or some of the organic components deposited on the catalyst surface.

Accordingly, the present invention also provides a process as described above in which all or part of the gaseous substream T(6) from step (iii) is recirculated to step (i).

The substream T(3) from step (iv) or step (c) is reacted in a further step (v) or step (g) with the substream T(4) from step (ii) or step (e) to give propylene oxide.

However, the gas phase T(6*a*) from step (e) of the process of the present invention can also be recirculated directly in a further step (f) to the step (a). In this case, the substream T(6*a*) comprises the components propane, oxygen and hydrogen in a molar ratio $C_3:O_2:H_2$ of 1:0.01–1:0–2, preferably in a molar ratio $C_3:O_2:H_2$ of 1:0.03–0.3:0–0.6 and particularly preferably in a molar ratio $C_3:O_2:H_2$ of 1:0.04–0.2:0–0.4.

The reaction of the propane-rich substream T(3) with the substream T(4) which is rich in hydrogen peroxide to give propylene oxide can be carried out by means of all methods known to those skilled in the art.

For the purposes of the present invention, the reaction in step (v) or step (g) is preferably the epoxidation of the propene from substream T(3) by means of hydrogen peroxide from substream T(4) in the presence of a catalyst to form propylene oxide.

Possible methods of carrying out the epoxidation in question and preferred epoxidation catalysts are described, inter alia, in DE 101 35 296.4, DE 101 05 528.5, DE 100 32 884.9, DE 101 55 470.2, DE 101 37 543.3 and DE 101 35 296.4.

Epoxidation catalysts which are particularly preferably used for the purposes of the invention are Ti-zeolites having the MFI or MEL structure or an MFI/MEL mixed structure, Ti-containing zeolite catalysts designated as TS-1, TS-2, TS-3, and also Ti zeolites having a framework structure isomorphous with β-zeolite.

Further details regarding the catalysts which can be used, in particular zeolites, may be found in, for example, DE 100 10 139.2, DE 197 23 950.1 and DE 102 32 406.9 and the prior art cited therein.

Accordingly, the present invention also provides a process of the abovementioned type in which the reaction in step (v) is the epoxidation of the propene from substream T(3) by means of hydrogen peroxide from substream T(4) in the presence of a catalyst to give propylene oxide.

In the process of the present invention, the degree of conversion into propylene oxide is at least 80%, preferably at least 85%, particularly at least preferably 95%.

The propylene oxide can be separated off from the mixture formed in the reaction in step (v) or step (g) by all methods known to those skilled in the art and can, if appropriate, be worked up further. Separation methods and work-up processes which are preferred for the purposes of the invention are described in DE 198 35 907.1 and DE 100 01 401.1.

The mixture obtained in addition to propylene oxide in step (v) or step (g) can be recirculated wholly or partly as substream T(7) comprising at least propane and propene to step (i) or step (a).

Accordingly, the present invention also provides a process of the above-described type in which all or part of a substream T(7) comprising at least propane and propene and having a ratio of propane to propene of less than 1 which comes from step (v) or step (g) is recirculated, if desired after a further work-up step, to step (i) or step (a), or else is recirculated directly to step (iv) or step (c).

The work-up step in question can be carried out by methods known to those skilled in the art, for example distillation, rectification or membrane separation.

Tables 1 and 2 below illustrate possible embodiments of the process of the present invention, with Table 1 relating to the integrated process which is shown schematically in FIG. 1 and Table 2 relating to the extended integrated process which is shown schematically in FIG. 2.

LIST OF REFERENCE NUMERALS

FIG. 1
Step (i) dehydrogenation of propane
Step (ii) condensation
Step (iii) synthesis of hydrogen peroxide
Step (iv) fractionation
Step (v) synthesis of propylene oxide
Step (vi) combustion
T(0), T(1), T(2), T(3) substreams
T(4), T(5), T(6), T(7)
X air or oxygen
Y propylene oxide
Z hydrogen FIG. 2
p Step (a) dehydrogenation of propane
p Step (b) condensation
p Step (c) fractionation
p Step (d) separation
p Step (e) synthesis of hydrogen peroxide
p Step (f) recirculation
p Step (g) synthesis of propylene oxide
T(0), T(1), T(2), T(3) substreams
T(4), T(5), T(5*a*), T(5*b*),
T(6*a*), T(7)
X oxygen
Y propylene oxide
Z hydrogen

We claim:
1. An integrated process for the synthesis of propylene oxide, comprising the following steps:
  (a) dehydrogenation of propane to give a substream T(0) comprising propane, propene and hydrogen;
  (b) fractionation of the substream T(0) to give at least one gaseous hydrogen-rich substream T(2) and a substream T(1) comprising propene and propane;

(c) fractionation of the substream T(1) to give at least one propane-rich substream T(5) and at least one propene-rich substream T(3);
(d) separation of the substream T(5) into at least the substreams T(5*a*) and T(5*b*);
(e) synthesis of hydrogen peroxide using the substream T(2) which is combined with at least the substream T(5*a*), giving a substream T(4) which is rich in hydrogen peroxide and a gaseous substream T(6*a*);
(f) at least partial recirculation of the substream T(6*a*) to step (a);
(g) reaction of the at least one substream T(3) with substream T(4) to give propylene oxide.

2. The process as claimed in claim 1, wherein the propane-rich substream T(5*b*) is fed to step (a).

3. The process as claimed in claim 1, wherein substream T(4) comprises hydrogen peroxide and water.

4. The process as claimed in claim 1, wherein the reaction in step (g) is the epoxidation of the propene from substream T(3) by means of hydrogen peroxide from substream T(4) in the presence of a catalyst to give propylene oxide.

5. The process as claimed in claim 1, wherein a substream T(7) comprising propane and/or propene is obtained from step (g) and is wholly or partly recirculated to step (a).

6. The process as claimed in claim 5, wherein the propane-rich substream T(5*b*) is fed to step (a), wherein a substream T(7) comprising propane and propene and having a ratio of propane to propene of less than 1 is obtained from step (g) and is, if appropriate after a further work-up step, wholly or partly recirculated to step (c).

7. The process as claimed in claim 1, wherein a substream T(7) comprising propane and propene and having a ratio of propane to propene of less than 1 is obtained from step (g) and is, if appropriate after a further work-up step, wholly or partly recirculated to step (c).

8. An integrated process for the synthesis of propylene oxide, comprising the following steps:

(a) dehydrogenation of propane to give a substream T(0) comprising propane, propene and hydrogen;
(b) fractionation of the substream T(0) to give at least one gaseous hydrogen-rich substream T(2) and a substream T(1) comprising propene and propane;
(c) fractionation of the substream T(1) to give at least one propane-rich substream T(5) and at least one propene-rich substream T(3);
(d) separation of the substream T(5) into at least the substreams T(5*a*) and T(5*b*);
(e) synthesis of hydrogen peroxide using the substream T(2) which is combined with at least the substream T(5*a*), giving a substream T(4) which is rich in hydrogen peroxide and a gaseous substream T(6*a*);
(f) at least partial recirculation of the substream T(6*a*) to step (a);
(g) reaction of the at least one substream T(3) with substream T(4) to give propylene oxide,
wherein the propane-rich substream T(5*b*) is fed to step (a) and wherein a substream T(7) comprising propane and/or propene is obtained from step (g) and is wholly or partly recirculated to step (a).

9. The process as claimed in claim 8, wherein a substream T(7) comprising propane and propene and having a ratio of propane to propene of less than 1 is obtained from step (g) and is, if appropriate after a further work-up step, wholly or partly recirculated to step (c).

10. The process as claimed in claim 8, wherein substream T(4) comprises hydrogen peroxide and water and wherein the reaction in step (g) is the epoxidation of the propene from substream T(3) by means of hydrogen peroxide from substream T(4) in the presence of a catalyst to give propylene oxide.

* * * * *